United States Patent [19]

Matsumura

[11] 4,279,478

[45] Jul. 21, 1981

[54] EYE EXAMINING INSTRUMENT

[75] Inventor: Isao Matsumura, Yokosuka, Japan

[73] Assignee: Canon Kabushiki Kaisha, Tokyo, Japan

[21] Appl. No.: 948,885

[22] Filed: Oct. 5, 1978

[30] Foreign Application Priority Data

Oct. 5, 1977 [JP] Japan ................................. 52-119697
Oct. 6, 1977 [JP] Japan ................................. 52-120414

[51] Int. Cl.³ ..................... A61B 3/10; G03B 29/00
[52] U.S. Cl. ........................................ 351/13; 351/14; 351/16; 354/62
[58] Field of Search ................... 351/6, 7, 13, 16, 14; 354/62

[56] References Cited

U.S. PATENT DOCUMENTS

| | | | |
|---|---|---|---|
| 3,288,546 | 11/1966 | Gans | 351/24 |
| 3,454,331 | 7/1969 | Maitenaz | 351/7 |
| 3,536,383 | 10/1970 | Cornsweet et al. | 351/16 |
| 3,746,432 | 7/1973 | Mason | 351/6 |
| 3,925,793 | 12/1975 | Matsumura et al. | 354/62 |
| 4,169,664 | 10/1979 | Bailey | 351/24 X |

Primary Examiner—John K. Corbin
Assistant Examiner—Rodney Bovernick
Attorney, Agent, or Firm—Fitzpatrick, Cella, Harper & Scinto

[57] ABSTRACT

A fixation object for maintaining the direction of the line of vision of an eye to be examined and a bright test object movable in a plane conjugate with the fundus of the eye with respect to an observation optical system are provided. A partial beam split from a beam emitted from the test object or a beam emitted from an auxiliary lamp cooperating with the test object is guided to an image pick-up tube for detecting the eye fundus image formed through the observation optical system. Further, recording paper and a marker cooperating with the test object are provided for memorizing the position of the test object each time the examination of an eye is completed. The images of the marks recorded on the recording paper are superposed on the eye fundus image and observed and photographed.

30 Claims, 20 Drawing Figures

EYE EXAMINING INSTRUMENT

BACKGROUND OF THE INVENTION

1. Field of the Invention

This invention relates to an instrument for examining the human eye and more particularly to an instrument for examining the retina of the eye.

2. Description of the Prior Art

As a method of detecting abnormality of a retina, examining the angle of view field has been practiced and a perimeter is generally used. As an example of the construction of the perimeter, there is well-known the one which is provided with a fixation object centrally on a semispherical screen and in which a test spot projected upon the screen is moved in radial direction. In this method, an isopleth over 360° is prepared by repeating the work of moving the spot light on the screen along a meridian, stopping the spot at a position whereat the subject exhibits a reaction and writing down that position on recording paper. The method of examining the view field now practiced has advanced from the examination of the limit of the visual recognition of a certain visible target, the width of such recognition, the degree or shape of the black spot to the expression of the degree or distribution of the photosensitivity of each region of the retina, the level of the sensitivity, etc. Where the minute portions of the retina are so discussed, the exact correspondence to the actual eye fundus becomes necessary. Heretofore, the relation with the region of the actual eye fundus has been inferred on an isopter having the examination result recorded on paper, but it is an inference to the last and assures no accuracy.

When examination is carried out, the subject is made to watch a fixation object to fix his line of vision and the examination is practised in such state. In that case, the portion of the retina which sees the fixation object is called the yellow spot which has the highest sensitivity on the retina. However, the region which gazes is not fixed where there is an eccentric fixation and it is possible that the subject looks aside from the fixation object and looks at the spot light during measurement, and it is desirable that this can be easily checked.

On the other hand, when developing a device for guiding the subjects line of vision by a retina camera disclosed in U.S. Pat. No. 4,068,932 (DOLS 2107788), the inventor has found that the technique is applicable to the measurement of the view field.

SUMMARY OF THE INVENTION

It is a first object of the present invention to enable a point on a retina stimulated to be displayed on the retina image which the examiner is observing.

It is a second object of the present invention to enable a mark representing the position being stimulated to be photographed in superposed relationship with the eye fundus image.

It is another object of the present invention to enable a mark or marks of the examination result regarding the portion whose examination has already been completed to be displayed on the retina image being observed.

It is still another object of the present invention to enable the marks (isopleth) of the examination result to be photographed in superposed relationship with the retina image after the examination has been completed.

The invention will become more fully apparent from the following detailed description thereof taken in conjunction with the accompanying drawings.

DESCRIPTION OF THE PREFERRED EMBODIMENTS

Of the embodiments which will hereinafter be disclosed, the embodiments shown in FIGS. 1 to 11 achieve the first and second objects of the invention, and the embodiments shown in FIGS. 13 to 20 achieve the other objects as well.

Figure 1:
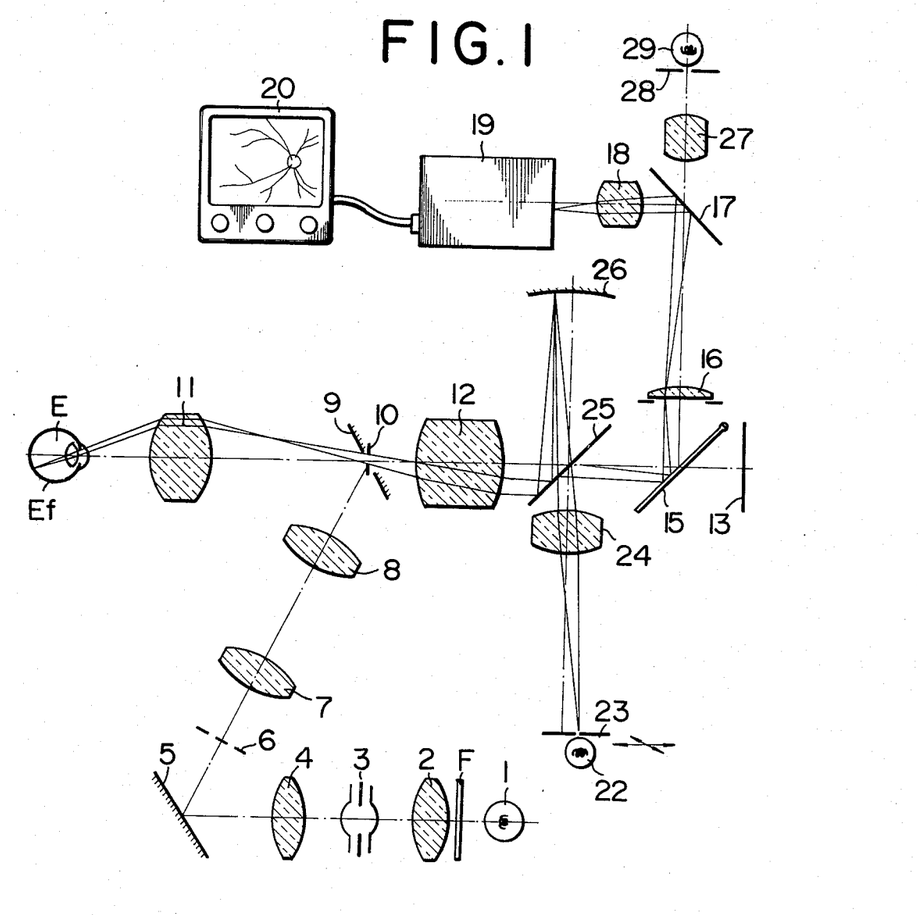
FIG. 1 is a side view showing a specific embodiment of the present invention.

FIG. 1 shows an embodiment of the present invention. This embodiment uses infrared rays as the eye fundus illuminating light beam, but as invisible rays, use may be made of a combination, for example, of weak light and high sensitivity image pick-up tube.

Figure 2:
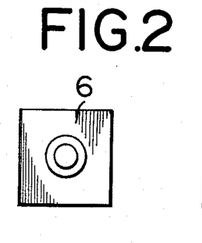
FIGS. 2 to 5 are plan views showing the component parts of the specific embodiment.
Figure 3:
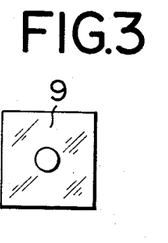

In FIG. 1, E designates an eye to be examined, and Ef is an eye fundus (retina). Denoted by 1 is a tungsten lamp which provides an illuminating light source. Denoted by 2 is a condenser lens, and 3 a strobo tube which is a light source for photography. Numeral 4 designates another condenser lens, and 5 a mirror for bending the light path. Designated by 6 is a ring slit plate provided with a ring-shaped opening, and a plan view thereof is shown in FIG. 2. The ring slit plate is conjugate with the light source 1 with respect to the condenser lens 2 and strobo tube 3, and also conjugate with the light source 3 with respect to the condenser lens 4.

Numerals 7 and 8 denote relay lenses and numeral 9 denotes an apertured mirror formed with a central opening. The portion of the mirror 9 surrounding the opening is a mirror surface which is conjugate with the ring slit plate 6 with respect to the relay lenses 7 and 8. Designated by 10 is an aperture diaphragm which cooperates with the ring slit plate 6 to prevent reflection by the retina, as is well-known.

Numeral 11 denotes an objective lens and 12 a group of focusing lenses. These lenses are arranged with their optical axes aligned together. The image is once focused by the objective lens, and then the light beam passed through the diaphragm 10 is again focused on an image plane 13 by the group of focusing lenses. A photographic film is disposed on the image plane 13.

Designated by 15 is a jump mirror and 16 a field lens. The field lens 16 is disposed conjugate with the image plane 13 with respect to the mirror surface of the jump mirror. Numeral 17 designates a half-mirror for bending the light path, 18 an image pick-up lens, and 19 an image pick-up tube having sensitivity to infrared wavelength as well. The light receiving surface of the image pick-up tube is conjugate with the image plane on the field lens with respect to the image pick-up lens 18. Denoted by 20 is a Braun tube (cathode ray tube) to which the output of the image pick-up tube 19 is applied through a processing circuit, not shown. A member F disposed between the observation light source 1 and the condenser lens 2 is an infrared filter for intercepting visible light and for passing there through infrared light.

Figure 4:
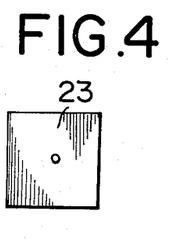

Numeral 22 designates a tungsten lamp and numeral 23 denotes a douser formed with a tiny opening, as shown in FIG. 4. The lamp 22 and the douser 23 together constitute a test object for measuring the view field, and are movable to right and left in the drawing or in a direction perpendicular to the plane of the drawing. Instead of the lamp and the douser, use may be made of a small-dimensioned light-emitting diode.

Denoted by 24 is a projection lens and 25 a half-mirror such as pellicle mirror. Numeral 26 denotes a concave spherical mirror. The concave spherical mirror 26 is substantially conjugate with the image plane with respect to the half-mirror 25, and the projection lens 24 combines together the douser 23 and the image plane 13 conjugately, as a result of which the light beam of the light flux emitted from the test object which is passed through the half-mirror is focused on the concave spherical mirror while the light beam reflected by the half-mirror is reflected by the jump mirror 15 and focused on the field lens 16.

Figure 5:
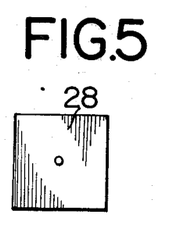

Designated by 27 is a projection lens, 28 a douser formed with a tiny opening as shown in FIG. 5, and 29 a tungsten lamp. The lamp 29 and the douser 28 together constitute a fixation object. The light beam emitted from the fixation object is focused on the image plane of the field lens 16 by the action of the projection lens 27. The fixation object may be caused to flicker in order to continue a steady gaze. A fixation object disposed outside the instrument may be watched by the eye being not examined, but the measurement accuracy is enhanced when the fixation object is watched by the eye being examined.

Why the mirror 26 is formed as a concave surface instead of planar surface is to provide an action corresponding to a field lens, but the concave mirror 26 may be replaced by a reflective diffusing plate.

In the above-described construction, when the lamps 1, 22 and 29 are turned on and the television set is driven, the image of the eye fundus and the image of the test object are projected on the Braun tube 20.

Only the infrared ray of the raditions from the tungsten lamp 1 is passed through the filter F and focused on the ring slit plate 6 by the converging action of the condenser lenses 2 and 3 and the reflecting action of the mirror 5. The infrared beam passed through the ring-shaped opening in the ring slit plate forms an image of the ring opening substantially on the mirror surface of the apertured mirror 9 due to the action of the relay lenses 7 and 8, and is reflected thereby to form an opening image again in the vicinity of the pupil or retina of the eye E to be examined due to the objective lens 11, whereafter it uniformly illuminates the eye fundus.

The object light emitted from the illuminated eye fundus leaves the eye to be examined and is focused by the objective lens 11, whereafter it passes through the diaphragm 10 and is converged by the group of focusing lenses 12, and then passes through the half-mirror 25 and is reflected by the jump mirror 15, and once forms an eye fundus image on the field lens 16, whereafter it is reflected by the half-mirror 17 and focused on the light receiving surface of the image pick-up tube 19 by the action of the image pick-up lens 18. Therefore, an eye fundus image is displayed on the Braun tube 20, but if the image is blurred, focus adjustment is effected by finely moving the whole or part of the focusing lens group 12 in the direction of its optic axis.

The light beam having left the opening 23 illuminated by the lamp 22 is converged by the projection lens 24 and enters the half-mirror 25, and part of the light is passed therethrough and the remainder of the light is reflected thereby.

The passed light beam is converged onto the concave mirror 26 and reflected by the mirror surface thereof and further reflected by the half-mirror 25 and converged by the focusing lens group, and passed through the diaphragm 10 and once converged and enters the objective lens 11, whereby it is converged to form the image of the test object 22, 23 on the eye fundus Ef of the eye being examined and stimulate that portion of the eye, so that the subject recognizes the test object. The remainder of the light beam is reflected by the half-mirror 25, whereafter it is reflected by the jump mirror 15 and once focused in the neighborhood of the field lens 16, and then reflected by the half-mirror 17 and forms the image of the test object 22, 23 on the light receiving surface of the image pick-up tube 19 with the aid of the image pick-up lens 18. In that case, the position occupied by the image of the test object projected onto the eye fundus Ef and the position of the image of the test object appearing on the eye fundus image displayed on the Braun tube are exactly coincident with each other.

The light beam emitted from the fixation object 28, 29 is converged by the focusing lens 27 and passed through the half-mirror 17 and focused on the image plane of the field lens, and then reflected by the jump mirror 15 and passed through the half-mirror 25, and further passed through the focusing lens 14, the diaphragm 10 and the objective lens 11 to form an image of the fixation object on the eye fundus Ef.

The position of the fixation object is suitably set on the optic axis, for example, the subject is made to watch the fixation object and fix his line of vision, and then the test object 22, 23 is moved from outside the view field toward the optic axis corresponding to the fixation point and when the subject sees the image of the test object, he informs of it and the test object is stopped at that position. At this time, the image of the object as well as the eye fundus image is displayed on the monitor, so that the operator can know to what part of the eye fundus image corresponds the position whereat the image of the object has come to halt.

Therefore, by dividing the entire circumference of the view field into several equal parts about the fixation point and repeating the above-described operation for each azimuth, separation can be substantially achieved between the region of the retina sensitive to light and the region of the retina which is not sensitive to light.

When the jump mirror 15 is caused to jump up with the image of the test object kept stationary and the strobo tube 3 is caused to flash, the photosensitive medium disposed on the image plane 13 is exposed to the light reflected from the eye fundus and at the same time, the light beam from the test object reflected by the half-mirror 25 is also focused onto the photosensitive medium 13, so that when developed, the photosensitive medium carries thereon the eye fundus image as well as the image of the test object.

It is to be noted that the infrared filter F may be shifted to the front of the strobo tube 3 and infrared film may be used as the photosensitive medium.

Figure 6:
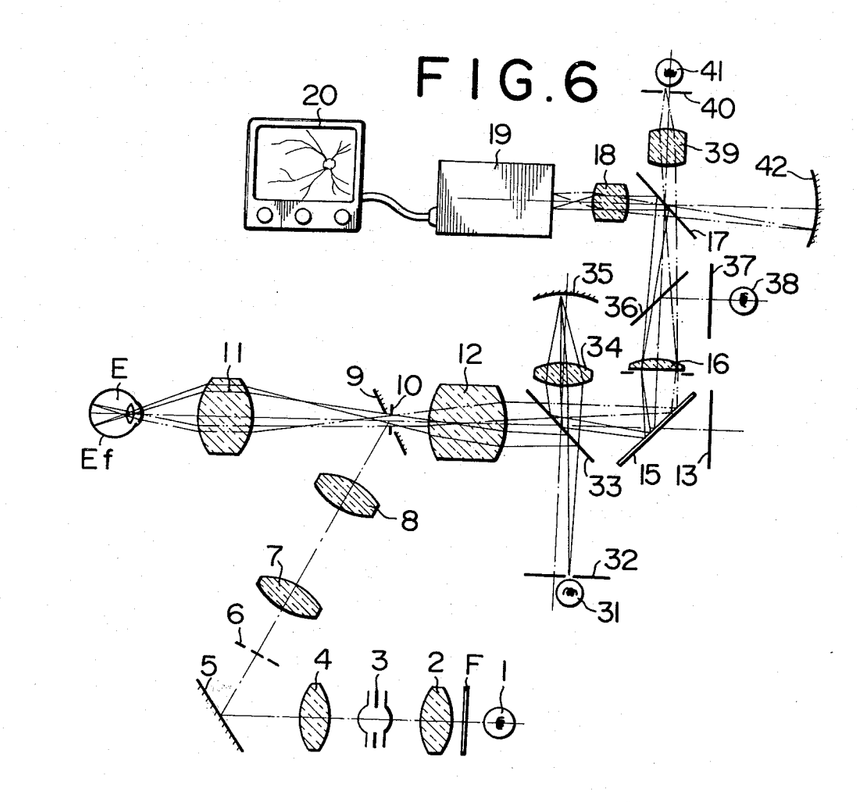
FIG. 6 is a side view showing another specific embodiment.

FIG. 6 shows another embodiment of the present invention in which the fixation object as well as movable object may be viewed on the Braun tube.

In FIG. 6, the eye fundus camera comprising elements 1 to 20 is equivalent to that of FIG. 1. The test object comprising a tungsten lamp 31 and a douser 32 provided with a marker opening is movable in the plane in which it is disposed. Numeral 33 designates a half-mirror, 34 a projection lens and 35 a concave mirror. The douser 32 and the image plane 13 of the focusing lens group are conjugate with respect to the half-mirror 33, and the douser 32 and the concave mirror 35 are conjugate with respect to the projection lens 34. Of the light flux emitted from the test object, the beam reflected by the half-mirror 33 is converged by the focusing lens group 12 and passed through the diaphragm 10 and once focused, whereafter it is again focused on the eye fundus Ef by the objective lens 11 and stimulates that portion of the eye. On the other hand, the light beam passed through the half-mirror 33 is focused on the concave mirror 35 by the projection lens 34 and reflected by the mirror 35 and enters the projection lens 34 in the direction opposite to the direction of the previous entry and converged thereby, whereafter it is reflected by the half-mirror 33 and further reflected by the jump mirror 15 and focused in the vicinity of the field lens 16. However, this light beam is focused on the image plane 13 when the jump mirror 15 jumps up.

The light beam passed through the field lens 16 is passed through the half-mirror 36 and reflected by the half-mirror 17, whereafter it is focused on the image pick-up surface of the image pick-up tube 19 by the focusing lens 18.

This focus position corresponds to the position whereat the light beam reflected by the half-mirror 33 is focused on the eye fundus, and appears on the image of the eye fundus.

Designated by 37 is a diffusing plate and 38 a lamp. The lamp 38 illuminates the diffusing plate 37. The diffused light emitted from the diffusing plate 37 is reflected by the half-mirror 36, whereafter it is passed through the field lens 16 and reflected by the jump mirror 15 and passed through the half-mirror 33 and further through the focusing lens group 14, the diaphragm and the objective lens 10 to illuminate the eye fundus with uniform brightness. This is the means for providing a suitable brightness of the back-ground for the movable object, and the brightness is variable as required.

Denoted by 40 is a douser having a tiny opening, and 41 a lamp. These two together constitute a fixation object. Designated by 39 is a projection lens which projects the image of the fixation object onto the image plane of the field lens 16, as the result of which the projected light beam goes back through the observation-picture-taking optical system so as to be focused on the eye fundus Ef. However, this light beam is one passed through the half-mirror 17, and the light beam reflected by this half-mirror 17 is focused on the concave mirror 42, whereby it is reflected and passed through the half-mirror 17 and focused on the image pick-up surface of the image pick-up tube by the image pick-up lens 18.

In the above-described arrangement and by turning on the lamps 31, 38 and 41 and moving the fixation object 40, 41 in the back-ground of a predetermined brightness, the line of vision of the subject is guided in the desired direction and fixed. At this time, a selected portion of the eye fundus is displayed on the monitor and the image of the fixation object also appears thereon.

With the subject watching the fixation object, the object 31, 32 is moved and the subject gives a sign when the object has come to a boundary between the position whereat it can be seen and the position whereat it cannot be seen, whereby the range of the view field can be detected. In that case, the object image superposed on the eye fundus image can be viewed on the monitor, and the object image superposed on the eye fundus image or only the object image can be photographed. Where the background illuminating means 37, 38 is incorporated in a device for illuminating the eye fundus with invisible light and converting the eye fundus image into a visible image by image pick-up means, the brightness of the background can conveniently be determined independently of the intensity of the light illuminating the eye fundus.

Figure 7:
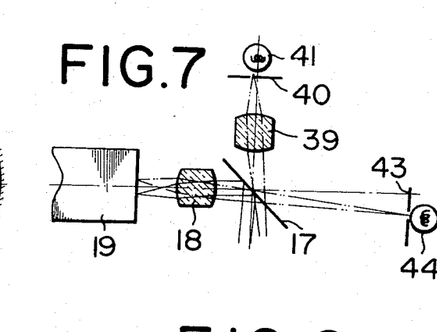
FIGS. 7 and 8 are side views showing essential portions of a modification of the FIG. 6 embodiment.

FIGS. 7 and 8 are fragmentary cross-sectional views showing a modified form of the essential portion of the FIG. 6 embodiment. The half-mirror 17, the image pick-up lens 18 or the image pick-up tube 19 in FIG. 7 corresponds to the half-mirror, the image pick-up lens or the image pick-up tube of FIG. 6. In this partial modification, a douser 43 provided with a tiny opening and a lamp 44 are provided in place of the concave mirror 42, and the douser 43 and the lamp 44 are operatively associated with the fixation object 40, 41 so as to have a function similar to the light beam reflected by the concave mirror 42 of FIG. 6. Thus, the light beam emitted from the fixation object is directed toward the eye bottom through the half-mirror 17, while the light beam emitted from the opening in the douser 43 illuminated by the lamp 44 is passed through the half-mirror 17 and forms the image of the opening on the image pick-up tube 19 by the picture-taking lens 18.

Figure 8:
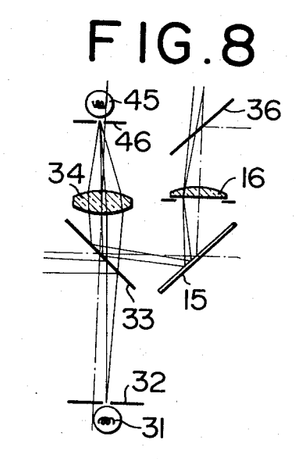

The jump mirror 15 and the half-mirror 33 in FIG. 8 correspond to the jump mirror and the half-mirror of FIG. 6. An auxiliary light source comprising a lamp 45 and a douser 46 provided with a tiny opening is operatively associated with the test object so as to have a function similar to the light beam reflected by the concave mirror 35. The light beam emitted from the auxiliary light source is converged by the projection lens 34 and reflected in succession by the half-mirror 33 and the jump mirror 15 and directed toward the image pick-up tube so as to form the image of the auxiliary light source on the portion of the eye fundus image corresponding to that portion of the eye fundus whereat the test object is focused.

Figure 9:
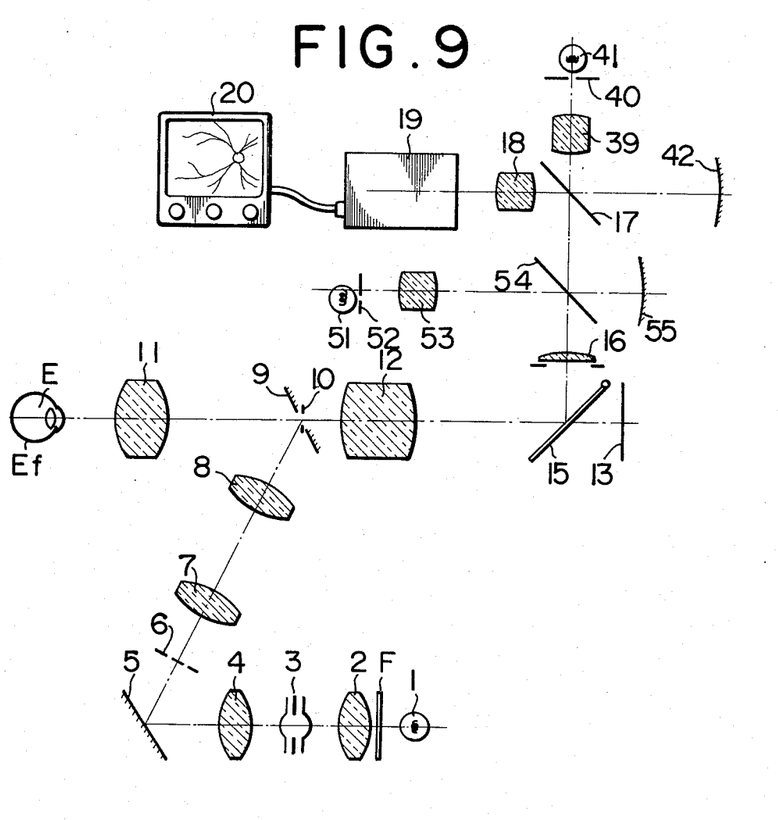
FIG. 9 is a side view showing still another specific embodiment.

FIG. 9 shows another embodiment. The members in this embodiment similar to those in the above-described embodiments are given similar reference characters. A test object comprising a lamp 51 and a douser 52 provided with a tiny opening is movable in a plane perpendicular to the optic axis, and a picture-taking lens 53 causes the light beam emitted from the test object to be reflected by the half-mirror 54 so as to be focused on the field lens 16 (the image plane of the focusing lens group 14).

The focused light beam is reflected by the jump mirror 15 and passed through the focusing lens group 12, the diaphragm 10 and the objective lens 11 so as to be focused on the eye fundus Ef and recognized by the subject.

On the other hand, the object light beam passed through the half-mirror 54 is focused on a concave mirror 55 and reflected thereby to go back along the light path and reflected by a half-mirror 54, whereafter it is reflected by the half-mirror 17 and focused on the image pick-up tube 19 by the image pick-up lens 18. Thus, the test object 51, 52 may be moved to effect the detection of the view field. The function of the fixation object comprising members 40 and 41 has already beam described and need not be described further. In the embodiment now under discussion, the position of the test object for measuring the view field and the position of the fixation object can be replaced by each other.

Figure 10:
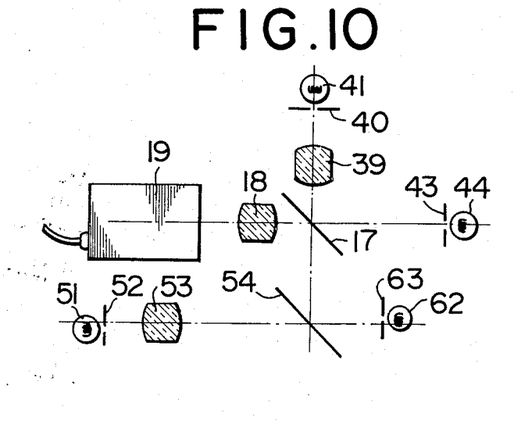
FIG. 10 is a side view showing essential portions of a modification of the FIG. 9 embodiment.

FIG. 10 shows essential portions of a partly modified form of the FIG. 9 embodiment. Here, the half-mirror 17 or the image pick-up tube 19 correspond to those of FIG. 9, and the mirror 42 of FIG. 9 is replaced by an auxiliary light source comprising a lamp 44 and a douser 43, and such auxiliary light source is operatively associated with the fixation object 40, 41 in a predetermined relationship.

Also, the concave mirror 55 of FIG. 9 is replaced by an auxiliary light source comprising a lamp 62 and a douser 63 and operatively associated with the test object 51, 52 in a predetermined relationship.

Thus, the light beam emitted from the test object 51, 52 is reflected toward the eye fundus by the half-mirror 54 while the light beam emitted from the auxiliary light source 62, 63 is reflected in the opposite direction toward the image pick-up tube by the half-mirror 54. Also, the light beam emitted from the fixation object 40, 41 is passed through the half-mirror toward the eye fundus, while the light beam emitted from the auxiliary light source 43, 44 is passed through the half-mirror 17 toward the image pick-up tube. Thus, the images of the respective auxiliary light sources are formed at the respective positions on the eye fundus image corresponding to the position of the mark or the fixation object image focused on the eye fundus.

Figure 11:
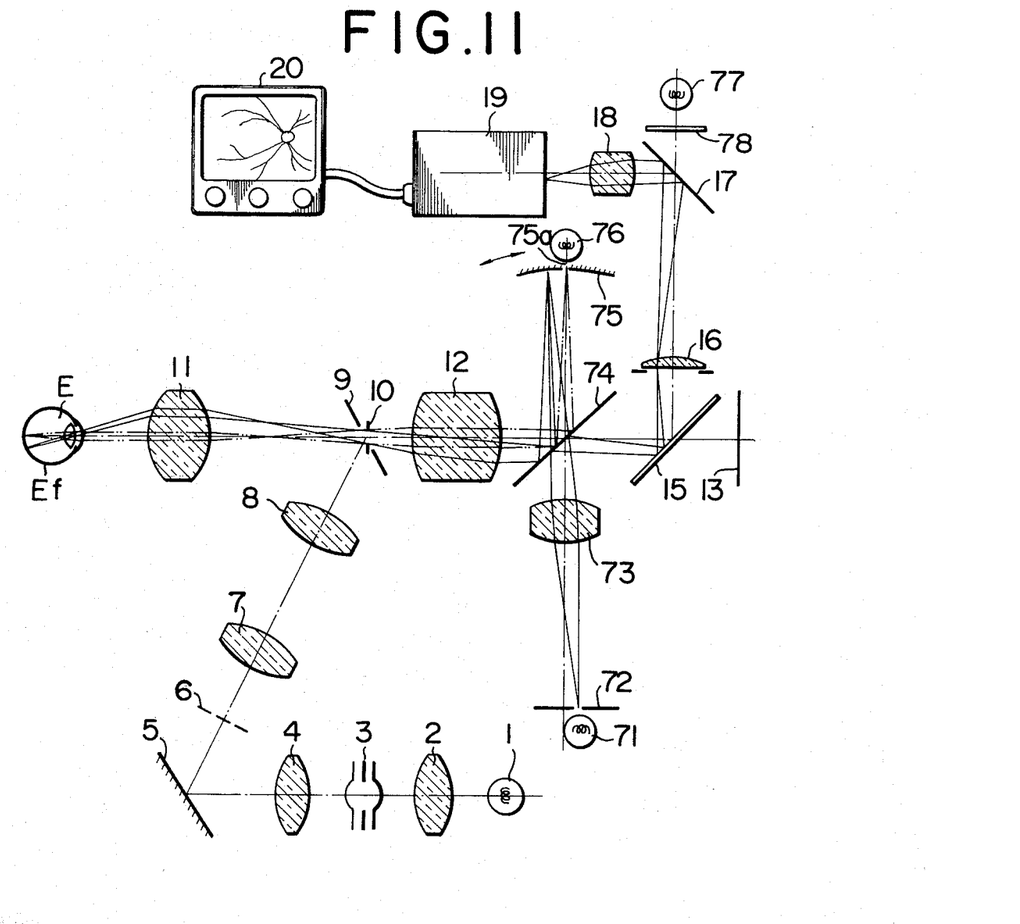
FIG. 11 is a side view showing a further embodiment.

FIG. 11 shows still another embodiment. In FIG. 11, members 1 to 20 are identical to those in the described embodiments and these together constitute an eye examining instrument. The image pick-up tube in this embodiment employs a conventional vidicon having sensitivity to visible range.

Figure 12:
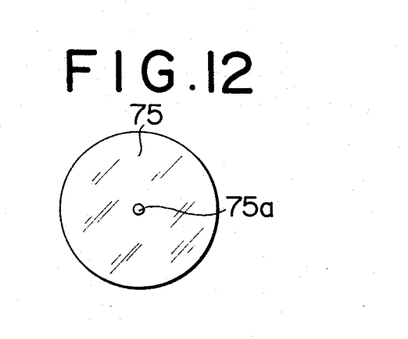
FIG. 12 is a plan view of component parts of the FIG. 11 embodiment.

A lamp 71 and a douser 72 provided with a tiny opening constitute a test object. Designated by 73 is a projection lens, and 74 a thin half-mirror disposed obliquely with respect to the optic axis of the observation-picture-taking optical system. Denoted by 75 is a concave mirror which is supported as by a gimbal (Cardan) mechanism so as to be rotatable about the center of curvature thereof. For example, at the center of a concave mirror 75, a tiny opening 75a is formed as shown in FIG. 12, and a lamp 76 swingable with the concave mirror is disposed behind the tiny opening. The lamp 76 and the tiny opening 75a together constitute a fixation object.

The concave mirror 75 is disposed conjugate with the image plane 13 of the focusing lens group 14 with respect to the half-mirror 74, and the test object 71, 72 and the concave mirror 75 are disposed conjugate with respect to the projection lens 73, as a result of which the light beam passed from the test object through the half-mirror 74 is once focused on the concave mirror 75, and reflected thereby and then by the back side of the half-mirror 74 and passed through the focusing lens group 14, the diaphragm 10 and the objective lens 11 and focused on the eye fundus Ef. On the other hand, the light beam passed from the test object and reflected by the half-mirror 74 is reflected by the inclined mirror 15, and then focused on the field lens 16 and reflected by the half-mirror 17 and focused on the light receiving surface of the image pick-up tube 19 by the image pick-up lens 18.

The light beam emitted from the fixation object 75a, 76 is reflected by the half-mirror 74 and converged by the focusing lens group 14 and passed through the diaphragm 10, whereafter it is once focused and then focused on the eye fundus Ef by the action of the objective lens 11.

The background illuminating means comprising a lamp 77 and a diffusing plate 78 illuminates the eye fundus Ef with a predetermined brightness through the half-mirror 17, the field lens 16, the inclined mirror 15, the half-mirror 74, the focusing lens group 12, the diaphragm 10 and the objective lens 11.

The half-mirror 17 may be disposed in the reversely inclined relationship and modification may be made so that the image plane on the field lens may be viewed through an eyepiece, and in such a case observation by the naked eyes can be carried out.

Operation of the above-described embodiments will now be explained. The lamps 1, 71, 76 and 77 are turned on and the television set is driven, whereupon the image of the test object is displayed on the Braun tube 20 with the image of the eye fundus. The operator adjusts the position of the fixation object 75a, 76 and fixes the line of vision of the subject to a desired position, and then moves the test object 71, 72 to measure the view field. The relation between this view field and the eye fundus can be known from the image displayed on the Braun tube. Film is disposed at the position of the image plane 13, the inclined mirror 15 is retracted out of the light path immediately before the strobo tube 3 flashes, the film is exposed to the light reflected by the eye fundus and the object light beam reflected by the half-mirror 74, and the display image indicating the position whereat the object is projected with the eye fundus is photographed.

Figure 13:
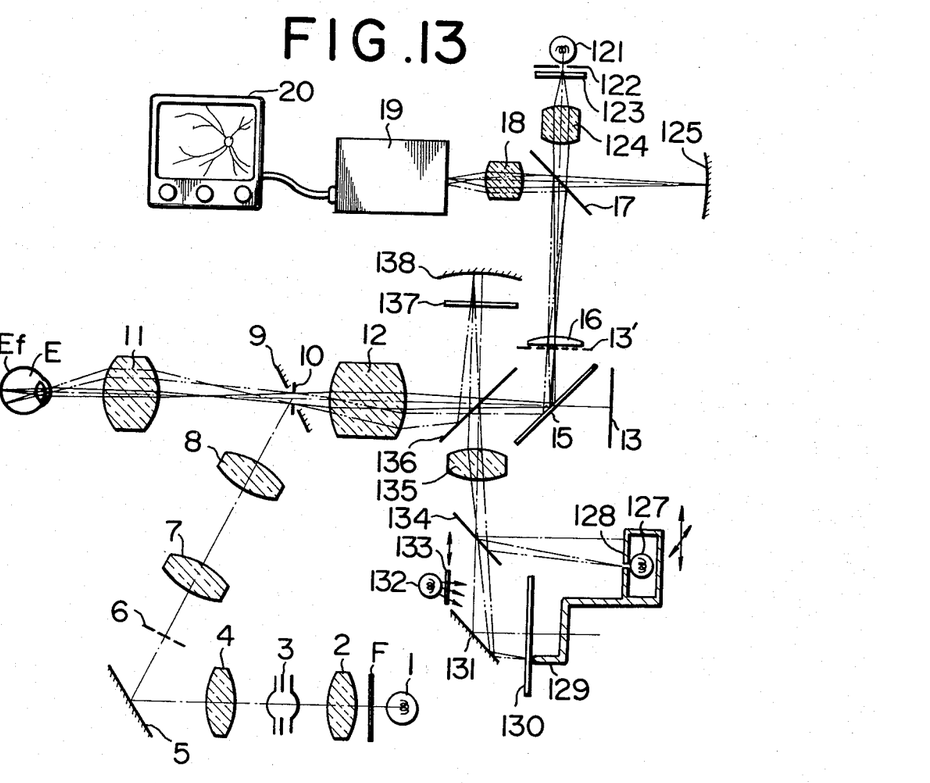
FIG. 13 is a side view showing still a further embodiment.
Figure 14:
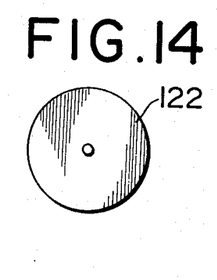
FIGS. 14, 15 and 16 are plan views showing component parts of the FIG. 13 embodiment.
Figure 15:
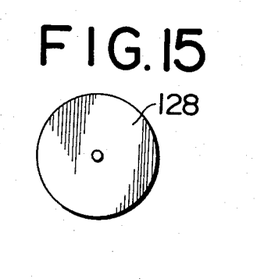
Figure 16:
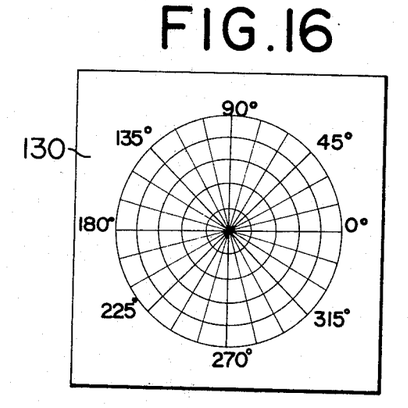

FIG. 13 shows a further embodiment of the present invention. Members 1 to 20 in FIG. 13 are similar to those in the described embodiments. Designated by 121 is a lamp, and 122 a douser provided with a tiny circular aperture (see FIG. 14). These together constitute a fixation object which is movable to the left and right in the drawing and in a direction perpendicular to the plane of the drawing. Denoted by 123 is a color filter which provides for a beam of different color depending on the usage. Denoted by 124 is a projection lens which functions to focus the light beam emitted from the fixation object on the image plane 13'. On the other hand, numeral 125 denotes a concave spherical mirror which is disposed conjugate with the image plane 13' with respect to the half-mirror 17, as a result of which it is conjugate with the image pick-up tube 19 with respect to the image pick-up lens 18. Why the mirror 125 is concave is to impart to it the action corresponding to the field lens. Designated by 127 is a lamp and 128 a douser having a tiny circular aperture (see FIG. 15). The lamp is housed within a housing and the douser is mounted to the housing. This lamp 127 and the douser 128 together constitute a test object which is movable with the housing vertically in the drawing and in a direction perpendicular to the plane of the drawing. Since the necessary amount of movement is very small, the housing may be moved by means of a reducing mechanism utilizing a linkage. Designated by 129 is a pen which is mounted to the housing having the test object and movable with the housing. Numeral 130 denotes a light transmitting plate on which a pattern as shown in FIG. 16 is depicted in white paint and which is arranged such that the center of the pattern is coincident with the optic axis. The pen 129 is so disposed that it can impart white marks on the light transmitting plate 130 as required.

Designated by 131 is a mirror for bending the light path, and this mirror bends the light path to align the test object and the direction of the pen. Denoted by 132 is a light source for illuminating the light-transmitting plate. Numeral 133 denotes an infrared filter which may be disposed in front of the light source during observation and removed during photography. Numeral 134 denotes a half-mirror, with respect to which the test object and the tip end of the pen 129 are conjugate. Denoted by 135 is a projection mirror, and 136 a half-mirror by which the projection lens 135 and the focusing lens group 12 are made conjugate.

Numeral 137 designates an interchangeable filter. A red, blue, green or transparent filter may be used as required. Designated by 138 is a concave mirror which is disposed conjugate with the image plane 13 with respect to the half-mirror 136 and also with the test object with respect to the projection lens 135.

Operation of the above-described apparatus will now be explained.

The subject is made to occupy a predetermined position, lamps 1, 121, 127 and 132 are turned on and the television set is driven. Of the radiations emitted from the lamp 1, only the infrared component is passed through the filter F and converged onto the ring-shaped slit 6 by the condenser lenses 2 and 3 and passed through the slit, whereafter it is caused to form the image of the slit on the apertured mirror 9 by the relay lenses 7 and 8 and is reflected thereby, and is focused in the vicinity of the pupil of the eye E being examined, by the objective lens 11, whereafter it illuminates the eye fundus Ef.

The infrared beam reflected by the eye fundus leaves the eye E and enters the objective lens 11 and is once converged, whereafter it passes through the diaphragm 10 and is converged by the focusing lens group 12, and passed through the half-mirror 36 and reflected by the inclined mirror 15 and focused on the image plane 13' and passed through the field lens 16 so as to be reflected by the half-mirror 17, whereafter it is focused on the image pick-up surface by the image pick-up lens 18. Thus, the eye fundus image is displayed on the monitor 20 and if the eye fundus image is blurred, the focusing lens group, for example, is finely adjusted for the focusing.

The light beam emitted from the fixation object is passed through the filter 123 and thereby becomes a colored light beam, and is converged by the image pick-up lens 124 and enters the half-mirror 17, by which it is separated into a transmitted light and a reflected light. The transmitted light is focused on the image plane through the field lens 16, whereafter it is reflected by the inclined mirror 15 and passed through the half-mirror 136 to enter the focusing lens group 12 and pass through the diaphragm 10, whereafter it is once focused and then focused on the eye fundus by the objective lens 11, and visually recognized by the subject. On the other hand, the light beam reflected by the half-mirror 17 is converged on the concave mirror 25 and reflected thereby and passed through the half-mirror 17 and focused on the image pick-up surface of the image pick-up tube 19 by the image pick-up lens 18, whereby it is displayed on the Braun tube. In the present case, the fixation object is adjusted onto the optic axis.

The light beam emitted from to test object 27, 28 is reflected by the half-mirror 34 and converged by the projection lens 35 and enters the half-mirror 36, whereby it is separated into a transmitted light and a reflected light. The transmitted light is converged on the concave mirror 38, by which it is reflected and further reflected by the half-mirror 36 and passed through the focusing lens group 12, the diaphragm 10 and the objective lens 11 to be focused on the eye fundus Ef. By the filter 37 in the light path, the beam is made into a predetermined color light. On the other hand, the light beam reflected by the half-mirror 36 is reflected by the jump mirror 15, whereafter it is focused on the image plane 13' and passed through the field lens 16, the half-mirror 17 and the image pick-up mirror 18 and focused on the image pick-up surface of the image pick-up tube 19, so that it is displayed on the Braun tube. At that time, the position whereat the image of the test object is formed on the eye fundus Ef is coincident with the position whereat the image of the test object appears on the eye fundus image displayed on the Braun tube.

When a white mark is imparted to the light-transmitting plate 130, the mark is illuminated by infrared light passed through the filter 133, so that the illuminating light is scattered and reflected back and reflected by the mirror 131 to pass through the half-mirror 134. In that case, the tip end of the pen 129 is conjugate with the test object 127, 128, so that the infrared light reflected by the mark follows the same light path as the light beam emitted from the test object and reflected by the half-mirror 136, and enters the image pick-up tube.

The reason why the light-transmitting plate is illuminated by infrared light is that if the light transmitting plate is illuminated by visible light, the light of the light beam scattered and reflected thereby which has been passed through the half-mirror enters the eye fundus and is visually recognized by the subject but the light-transmitting plate has already recorded thereon the result of the examination and the infrared light prevents such recorded information from being recognized by the subject to impede the examination.

Eye examination is started with the fixation object 121, 122 watched by the subject and whether the subject sees the fixation object by the portion of the yellow spot can be confirmed from the positional relation between the eye fundus image on the Braun tube and the image of the fixation object. With the fixation object watched by the subject, the test object 127, 128 is quietly moved from the marginal portion of the view field, for example, toward the center thereof and when the object is seen, the subject is made to give a sign, whereupon the object is fixed and the pen 129 is urged against the light-transmitting plate to impart a white mark thereto.

Figure 17:
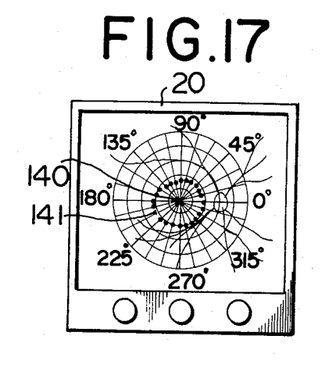
FIG. 17 shows a form of the image displayed on a cathode ray tube.

In that case, the position whereat the object is fixed can be observed on the Braun tube and thus, on the Braun tube shown in FIG. 17, the eye fundus image and the fixation object image 40 and the locus 41 of the object having Ep attached thereto are displayed.

When an examination of a range has been completed by the above-described operation, the same operation is repeated with the angle shifted slightly and the result over the whole circumference is recorded, whereby an isopter 141 is obtained. This isopter 141 can be observed as superposed on the eye fundus image and it is convenient to the diagnosis of a disease, but it would be more convenient if it could be recorded.

If the inclined mirror 15 is caused to jump up simultaneously with the flashing of the strobo tube 3 and the infrared filter 33 is removed from the front of the lamp 32, the visible light emitted from the strobo tube 3 follows the same light path as the light beam emitted from the observation light source 1 to illuminate the eye fundus and is reflected thereby, whereafter it passes through the objective lens 11, the diaphragm 10, the focusing lens group 12 and the half-mirror 36, and the film 13 is exposed to such light. At the same time, the light beam from the light-transmitting plate having recorded thereon the isopter is reflected by the mirror 131 and passed through the half-mirror 134 and converged by the projection lens 135 and reflected by the half-mirror 136, whereafter it forms the image of the isopter on the film 13. Thus, the isopter is photographed in superposed relationship with the eye fundus image.

Figure 18:
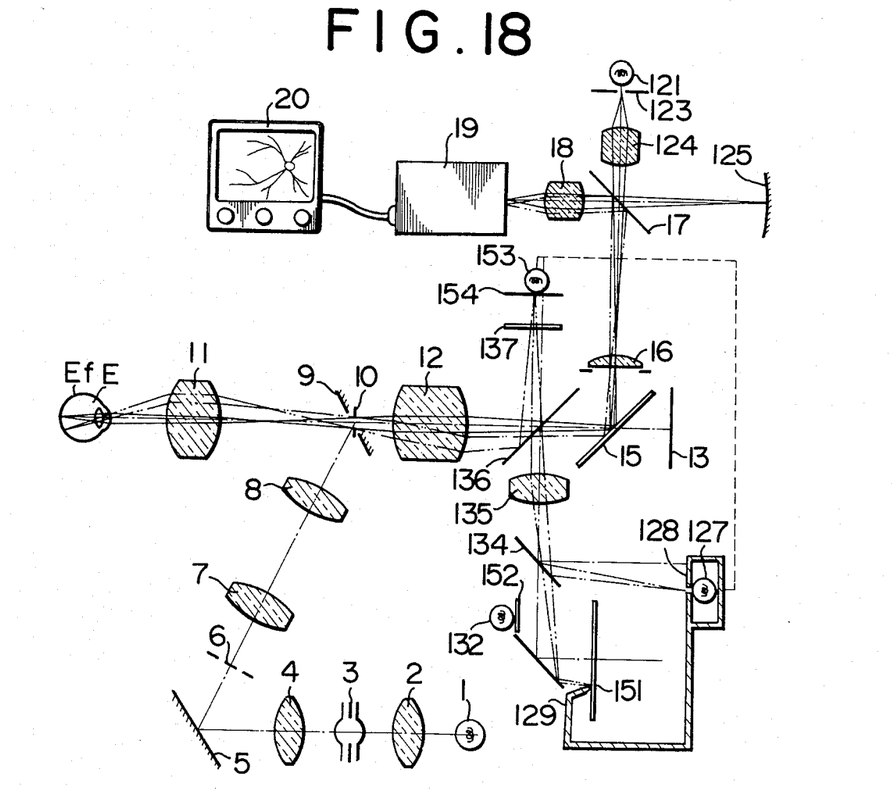
FIG. 18 is a side view showing a further embodiment.

FIG. 18 shows a further embodiment of the present invention. In FIG. 18, members similar to those in FIG. 13 are given similar reference numerals.

In this embodiment, black paper 151 is used as the medium for recording the record point of the examination result, and therefore the pen 129 imparts white marks in the direction opposite to that in the previous embodiment. Also, the patterns and characters depicted on the recording paper 151 are printed in white color.

Designated by 152 is a color filter equivalent to the filter 137. When the record point is photographed, a filter of the same color as that used for the examination may be mounted and the recording paper may be illuminated, whereby the record point of that color is photographed on the photographic film and this is convenient in that when a diagnosis is made later on the photograph, what color of test object was used in the examination can be known at a glance.

Also, an auxiliary test object comprising a lamp 153 and a douser 154 having a tiny opening is disposed instead of the concave mirror 138. This auxiliary test object provides for a light beam corresponding to the light beam emitted from the test object and reflected by the concave mirror, and it is operatively associated with the test object 127, 128. The light beam emitted from the auxiliary test object stimulates the eye fundus and the light beam emitted from the test object forms a spot image on the eye fundus image.

The illumination by the observation light source 1 may be utilized as a background illumination for the movable object.

Figure 19:
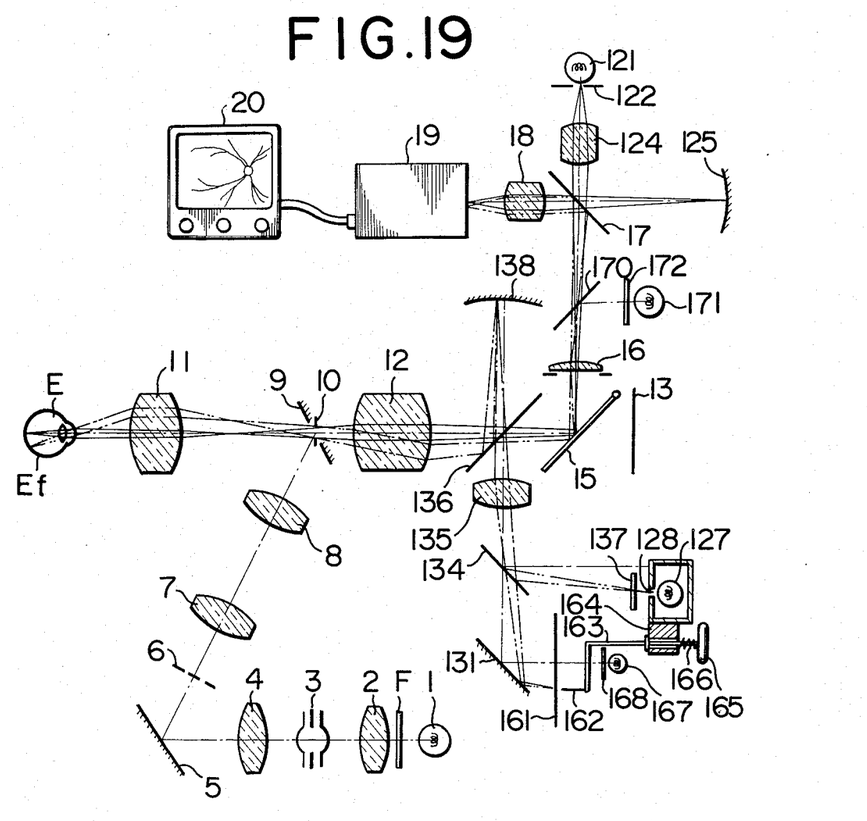
FIG. 19 is a side view showing a further embodiment.

FIG. 19 illustrates a further embodiment. Again in this Figure, members similar to those in FIG. 13 are given similar reference characters. In this embodiment the recording means is modified and black recording paper 161 is fixed under tension. Designated by 162 is a needle and 161 a slide bar. The needle is mounted on the slide bar, and the slide bar slides without rotating in a bearing 164 mounted on the housing of the test object. Denoted by 165 is a button which is secured to the other end of the slide bar 163. A compression coil spring 166 is inserted between the push button 165 and the bearing 164. Therefore, when the operator pushes in the button 165, the needle 162 can form an aperture in the recording paper 161 and this aperture makes a record point. Designated by 167 is a lamp provided for illuminating the recording paper 161 from the back thereof, and 168 is a removable infrared filter.

Reference numerals 170 to 172 designate means for imparting background illumination and reference numeral 170 denotes a half-mirror obliquely disposed in the light path. Designated by 171 is a light source whose quantity of light is adjustable, and 172 a diffusing plate. The light emitted from the diffusing plate uniformly illuminates the eye fundus through the field lens 16, the inclined mirror 15, the half-mirror 136, the focusing lens group 12, the diaphragm and the objective lens 11.

Figure 20:
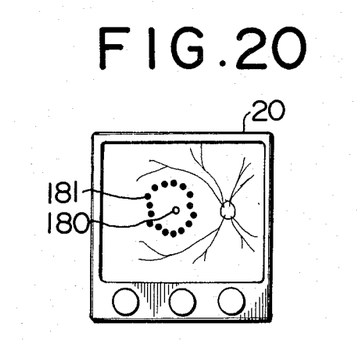
FIG. 20 shows a form of the image displayed on a cathode ray tube.

In the above-described arrangement, a locus by record points may be formed on the recording paper by repeating the work of imparting background illumination, causing the subject to watch the fixation object, moving the test object 127, 128, and pushing the button 165 at the recording position to form a tiny aperture in the recording paper 161. The recording paper 161 is illuminated by the illuminating light source, and the infrared light beam passed through each record point is reflected by the mirror 131, and passed through the half-mirror 134 and the projection lens 135, and reflected by the half-mirror 136 and the inclined mirror 115, and passed through the field lens 16 and the half-mirror 170 and reflected by the half-mirror 17, and forms each spot image on the light receiving surface of the image pick-up tube 19 with the aid of the image pick-up lens 18. Accordingly, on the Braun tube, the eye fundus image and the image 180 of the fixation object as well as the record points 181 are displayed as shown in FIG. 20. When the examination has been completed and the record points have made a round, the strobo tube 3 is caused to flash, the inclined mirror 15 is caused to jump up, the filter is removed and the film 13 is exposed to the light beam forming the eye fundus image and the light beam passed through the record points, whereby the locus of the record points can be photographed in superposed relationship with the eye fundus image.

According to the embodiments described in connection with FIGS. 13, 18 and 19, the image of the object being measured can be seen on the eye fundus image and in addition, the record points in the range for which the examination has been completed are displayed, and therefore, at what position the subject will give a sign can be foreseen from the manner of continuity of the record points, and this leads to the ease of examination and enhanced accuracy of the examination. On the other hand, when photography is effected, the eye fundus image and the locus of the record points can be photographed so that, when diagnosis is made on the photograph, the portion of the eye fundus and the position of the examination can be judged in exactly corresponding relationship.

What I claim:
1. An eye examining instrument comprising:

a photographic system for photographing an eye fundus, including objective optical means adapted to be opposed to a human eye, photosensitive means and observation means;

an illuminating system for illuminating the eye fundus;

a first projection system for projecting a test mark onto a desired position on the eye fundus and for moving the same along a desired path on the eye fundus;

a fixation object for fixing the line of vision of the eye; and a second projection system for projecting an indicative mark onto said photosensitive means during photography, said second projection system being coupled to said first projection system.

2. An instrument according to claim 1, wherein said first and second projection systems commonly have a test object for generating a visible beam forming a test mark on the eye fundus and a beam splitter.

3. An instrument according to claim 2, wherein said beam splitter is a pellicle mirror.

4. An instrument according to claim 1, wherein said first projection system includes a test object for generating a visible beam forming a test mark on the eye fundus, and said second projection system includes an auxiliary beam source for generating a beam forming said indicative mark and cooperable with said test object.

5. An instrument according to claim 1, further comprising means for memorizing the position whereat the test mark is projected onto the eye fundus, and for projecting beams on said photosensitive means.

6. An instrument according to claim 5, wherein said memorizing means includes a recording carrier, marking means for marking said carrier, and illuminating means for illuminating said carrier.

7. An instrument according to claim 1, wherein said observation means has image pick-up means and display means electrically coupled to said pick-up means, said first projection system includes a test object for generating a visible beam for forming a test mark on the eye fundus and beam splitting means disposed between said objective optical means and said image pick-up means, and further comprising:

memorizing means including a recording carrier, marking means cooperable with said test object to mark said carrier, and illuminating means for illuminating said carrier; and an image transmitting optical system for transmitting the beam from said recording carrier to said photosensitive means.

8. An instrument according to claim 7, wherein said illuminating means for illuminating said carrier generates a visible beam during photography and generates an invisible beam during observation.

9. An instrument according to claim 7, wherein said marking means includes an axially movable needle for forming apertures in said recording carrier.

10. An instrument according to claim 7, wherein the recording surface of said recording carrier is black and said marking means has a pen for writing in white paint on said recording surface.

11. An instrument according to claim 1, wherein said fixation object generates visible light and is coupled to light guiding means having said objective optical means.

12. An instrument according to claim 11, wherein said fixation object causes visible light to flicker.

13. An instrument according to claim 11, wherein said fixation object includes a light source and a removable colorable filter.

14. An eye examining method comprising the steps of:

illuminating the fundus of an eye to be examined and directing a beam reflected by the eye fundus to observation means through an objective optical system;

fixing the line of vision of said eye;

projecting a visible test beam stimulating the eye fundus onto the eye fundus through said objective optical system and scanning the eye fundus along one or more meridians;

projecting onto said observation means an indication beam cooperable with said test beam to scan;

memorizing the position on the eye fundus which has responded to said test beam; and observing the information memorized in superposed relationship with the image of the eye fundus and an indicative mark formed by said indication beam.

15. A method according to claim 14, further comprising the step of photographing the information memorized in superposed relationship with the image of the eye fundus.

16. A method according to claim 14, wherein the beam for illuminating the eye fundus is infrared light, and said observation means comprises sensing means sensitive to said infrared light and display means electrically coupled to said sensing means.

17. An eye examining instrument comprising:

a system for inspecting an eye, having photosensitive means for detecting an image of an eye fundus of an eye to be inspected;

observation means, optically coupled to said eye inspecting system, for observing the eye fundus;

an illumination system for illuminating the eye fundus to be inspected;

a projection system for scanningly projecting a test mark onto a desired position on the eye fundus and for optically stimulating the eye fundus along a desired path;

memorizing means for memorizing information relating to a particular position on the eye fundus to be inspected;

supplying means for supplying the information to superpose the information on the image of the eye fundus; and a fixation object for fixing the line of vision of the eye.

18. An instrument according to claim 17, wherein said memorizing means includes an information recording carrier, marking means for recording on said recording carrier cooperable with said scanning means, and an illuminating apparatus for illuminating said recording carrier.

19. An instrument according to claim 18, wherein said illuminating apparatus includes a light source and a removable color filter.

20. An instrument according to claim 17, wherein said observation means includes imaging lens means, image sensing means sensitive to an infrared beam, and display means electrically coupled to said image sensing means, and said illuminating system includes a source for emitting an infrared beam.

21. An instrument according to claim 17, wherein said eye inspecting system includes objective lens, said projection system includes said objective lens, and a light guiding system transmits the visible beam emitted from said fixation object to the image side surface of said objective lens.

22. An instrument according to claim 17, further comprising a background lighting apparatus optically coupled to said eye inspecting system.

23. An instrument according to claim 22, wherein said background lighting apparatus includes a light source and a diffusing plate.

24. An eye examining instrument comprising:
  an eye inspecting system adapted to face an eye to be examined;
  observation means, optically coupled to said eye inspecting system, for observing the eye fundus of the eye to be inspected;
  an illumination system for illuminating the eye to be inspected;
  a projection system for scanningly projecting a test mark onto a desired position on the eye fundus and for optically stimulating the eye fundus along a desired path;
  memorizing means for memorizing information relating to a particular position on the eye fundus to be inspected;
  supplying means for supplying the information to said observation means during observation of the eye fundus; and
  a fixation object for fixing the line of vision of the eye.

25. An instrument according to claim 24, wherein said memorizing means includes an information recording carrier, marking means for recording on said recording carrier cooperable with said projection system, and an illuminating apparatus for illuminating said recording carrier.

26. An instrument according to claim 25, wherein said illuminating apparatus includes a light source and a removable color filter.

27. An instrument according to claim 24, wherein said observation means includes imaging lens means, image sensing means sensitive to an infrared beam, and display means electrically coupled to said image sensing means, and said illuminating system includes a source for emitting an infrared beam.

28. An instrument according to claim 24, wherein said eye inspecting system includes an objective lens, said projection system includes said objective lens, and a light guiding system transmits the visible beam emitted from said fixation object to the image side surface of said objective lens.

29. An instrument according to claim 24, further comprising a background lighting apparatus optically coupled to said eye inspecting system.

30. An instrument according to claim 29, wherein said background lighting apparatus includes a light source and a diffusing plate.

* * * * *

UNITED STATES PATENT AND TRADEMARK OFFICE
CERTIFICATE OF CORRECTION

PATENT NO. : 4,279,478
DATED : July 21, 1981
INVENTOR(S) : ISAO MATSUMURA

It is certified that error appears in the above—identified patent and that said Letters Patent is hereby corrected as shown below:

Column 7, line 20, change "beam" to --been--.

Column 8, line 59, change "consitute" to --constitute--.

Column 10, line 17, change "to" to --the--.

Column 11, line 7, change "locus" to --focus--.

Column 12, line 23, change "locus" to --focus--; line 48, change "locus" to --focus--; line 62, change "locus" to --focus--.

Claim 21, line 66, after "includes" insert --an--.

Claim 18, line 53, change "scanning means" to --projection system--.

Signed and Sealed this

Third Day of November 1981

[SEAL]

Attest:

Attesting Officer

GERALD J. MOSSINGHOFF

Commissioner of Patents and Trademarks